US009885077B2

(12) United States Patent
Asogawa et al.

(10) Patent No.: US 9,885,077 B2
(45) Date of Patent: Feb. 6, 2018

(54) CHIP FOR ANALYSIS OF TARGET SUBSTANCE

(71) Applicant: NEC Corporation, Tokyo (JP)

(72) Inventors: Minoru Asogawa, Tokyo (JP); Hisashi Hagiwara, Tokyo (JP); Yoshinori Mishina, Tokyo (JP); Yasuo Iimura, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 15/130,601

(22) Filed: Apr. 15, 2016

(65) Prior Publication Data

US 2017/0022539 A1 Jan. 26, 2017

Related U.S. Application Data

(63) Continuation of application No. 14/386,527, filed as application No. PCT/JP2013/051332 on Jan. 23, 2013, now abandoned.

(30) Foreign Application Priority Data

Mar. 21, 2012 (JP) ................................. 2012-063645

(51) Int. Cl.
*B01L 3/00* (2006.01)
*G01N 27/447* (2006.01)
(Continued)

(52) U.S. Cl.
CPC .......... *C12Q 1/686* (2013.01); *B01F 11/0051* (2013.01); *B01L 3/502707* (2013.01);
(Continued)

(58) Field of Classification Search
None
See application file for complete search history.

(56) References Cited

U.S. PATENT DOCUMENTS

2005/0202504 A1* 9/2005 Anderson ........... B01F 11/0071
435/6.11
2009/0221091 A1 9/2009 Mogi et al.
(Continued)

FOREIGN PATENT DOCUMENTS

EP 1 563 907 A2 8/2005
GB 2 453 310 A 4/2009
(Continued)

OTHER PUBLICATIONS

Extended European Search Report dated Nov. 2, 2015, by the European Patent Office in counterpart European Patent Application No. 13764529.7.

(Continued)

*Primary Examiner* — Jennifer Wecker
(74) *Attorney, Agent, or Firm* — Finnegan, Henderson, Farabow, Garrett & Dunner, L.L.P.

(57) ABSTRACT

The present invention provides a chip for analysis of a target substance that is compact and allows analysis of a target substance with less time and effort. The chip for analysis of a target substance includes a first flexible substrate 1, a second flexible substrate 2, and a third substrate 3. A flow channel-forming non-bonded area 11 is formed on a bonding surface of the first flexible substrate 1 and the second flexible substrate 2 in a band-like manner and an extraction chamber-forming non-bonded area 5 having a wider band width than the flow channel-forming non-bonded area 11 is formed at a part of the flow channel-forming non-bonded area 11. The first flexible substrate 1 includes a through-hole 7 that is in contact with the flow channel-forming non-bonded area 11, a shutter-forming non-bonded area 12b is formed on a bonding surface of the second flexible substrate 2 and the third substrate 3 at a far side of the through-hole 7 relative to the extraction chamber-forming non-bonded area 5 such that the shutter-forming non-bonded area 12b and the flow (Continued)

channel-forming non-bonded area 11 intersect above and below, the first flexible substrate 1 and the second flexible substrate 2 include a pressure supply port 18*b* that comes through the substrates so as to be in contact with the shutter-forming non-bonded area 12*b*, and a magnetic particle 16 that binds to a target substance is placed above the extraction chamber-forming non-bonded area 5.

4 Claims, 5 Drawing Sheets (51) Int. Cl.
*G01N 27/453* (2006.01)
*C12Q 1/68* (2006.01)
*G01N 27/74* (2006.01)
*B01F 11/00* (2006.01)

(52) U.S. Cl.
CPC ... *B01L 3/502715* (2013.01); *B01L 3/502738* (2013.01); *B01L 3/502761* (2013.01); *G01N 27/44704* (2013.01); *G01N 27/44791* (2013.01); *G01N 27/453* (2013.01); *G01N 27/745* (2013.01); *B01L 2200/0668* (2013.01); *B01L 2300/0645* (2013.01); *B01L 2300/0816* (2013.01); *B01L 2300/0861* (2013.01); *B01L 2300/0864* (2013.01); *B01L 2300/0867* (2013.01); *B01L 2300/0874* (2013.01); *B01L 2300/0887* (2013.01); *B01L 2300/123* (2013.01); *B01L 2400/043* (2013.01); *B01L 2400/0481* (2013.01); *B01L 2400/0487* (2013.01); *B01L 2400/0655* (2013.01)

(56) References Cited

U.S. PATENT DOCUMENTS

| | | | |
|---|---|---|---|
| 2010/0221814 A1 | 9/2010 | Asogawa et al. | |
| 2010/0323432 A1* | 12/2010 | Asogawa | B01F 11/0071 435/287.2 |
| 2011/0000561 A1* | 1/2011 | Asogawa | B01L 3/50273 137/561 R |
| 2011/0005932 A1* | 1/2011 | Jovanovich | G01N 27/745 204/453 |
| 2011/0136179 A1* | 6/2011 | Bin/Lee | B01F 11/0071 435/91.2 |
| 2012/0023088 A1 | 9/2012 | Asogawa et al. | |
| 2014/0170641 A1* | 6/2014 | Macemon | G01N 1/00 435/5 |

FOREIGN PATENT DOCUMENTS

| | | |
|---|---|---|
| JP | 2005-224181 | 8/2005 |
| JP | 2009-247297 | 10/2009 |
| JP | 2010-145269 | 7/2010 |
| JP | 2011-237277 | 11/2011 |
| JP | 2011-242234 | 12/2011 |
| WO | WO 03/085379 A2 | 10/2003 |
| WO | WO 2007/064635 A1 | 6/2007 |
| WO | WO 2009/035061 A1 | 3/2009 |
| WO | WO 2009/038203 A1 | 3/2009 |
| WO | WO 2011/142085 A1 | 11/2011 |

OTHER PUBLICATIONS

Notification of Reasons for Refusal dated Dec. 22, 2015, by the Japanese Patent Office in counterpart Japanese Patent Application No. 2014-506059.

International Search Report dated Mar. 19, 2013, in corresponding PCT international application.

Notification of Reasons for Refusal dated May 23, 2017, by the Japanese Patent Office in counterpart Japanese Patent Application No. 2015-130157.

* cited by examiner

CHIP FOR ANALYSIS OF TARGET SUBSTANCE

CROSS-REFERENCE TO RELATED PATENT APPLICATIONS

This application is a continuation of U.S. patent application Ser. No. 14/386,527, filed Sep. 19, 2014, which is a National Stage Entry of International Application No. PCT/JP2013/051332, filed Jan. 23, 2013, which claims priority from Japanese Patent Application No. 2012-063645, filed Mar. 21, 2012. The entire contents of the above-referenced applications are expressly incorporated herein by reference.

TECHNICAL FIELD

The present invention relates to a chip for analysis of a target substance.

BACKGROUND ART

Conventionally, various kinds of DNA analyzers have been proposed (see, for example, Patent Document 1). Conventional DNA analyzers have been large analyzers in which reaction vessels, photodetectors, amplifiers, and the like are independently provided, respectively, and therefore have required wide installation spaces. Furthermore, conventional DNA analyzers have required great deal of time and efforts.

CITATION LIST

Patent Document(s)

Patent Document 1: JP 2009-247297 A

SUMMARY OF INVENTION

Problem to be Solved by the Invention

Hence, the present invention is intended to provide a chip for analysis of a target substance that is compact and allows analysis of a target substance such as DNA with less time and effort.

Means for Solving Problem

In order to achieve the above object, the present invention provides a first chip for analysis of a target substance, including:
a laminate, the laminate including:
a first flexible substrate;
a second flexible substrate; and
a third substrate, wherein
a flow channel-forming non-bonded area is formed on a bonding surface of the first flexible substrate and the second flexible substrate in a band-like manner and an extraction chamber-forming non-bonded area having a wider band width than the flow channel-forming non-bonded area is formed at a part of the flow channel-forming non-bonded area,
the first flexible substrate includes a through-hole that is in contact with the flow channel-forming non-bonded area,
a shutter-forming non-bonded area is formed on a bonding surface of the second flexible substrate and the third substrate in a band-like manner at a far side of the through-hole relative to the extraction chamber-forming non-bonded area such that the shutter-forming non-bonded area and the flow channel-forming non-bonded area intersect above and below via the second flexible substrate being interposed therebetween,
at least one of both of the first flexible substrate and the second flexible substrate and the third substrate includes a pressure supply port that comes through the substrate(s) so as to be in contact with the shutter-forming non-bonded area,
a magnetic particle that binds to a target substance is placed above the extraction chamber-forming non-bonded area,
a flow channel and an extraction chamber are formable by supplying pressure from the through-hole to raise a site above the flow channel-forming non-bonded area and a site above the extraction chamber-forming non-bonded area,
the flow channel is blockable by supplying pressure from the pressure supply port to raise a site above the shutter-forming non-bonded area, and
the target substance that is bound to the magnetic particle is capturable by generating a magnetic field at at least one of an undersurface of the third substrate directly below an end of the extraction chamber at the opposite side of the through-hole and a top surface of the first flexible substrate directly above an end of the extraction chamber at the opposite side of the through-hole.

The present invention also provides a second chip for analysis of a target substance, including:
a laminate, the laminate including:
a first flexible substrate;
a second flexible substrate; and
a third substrate, wherein
a flow channel-forming non-bonded area is formed on a bonding surface of the first flexible substrate and the second flexible substrate in a band-like manner and a mixing chamber-forming non-bonded area having a wider band width than the flow channel-forming non-bonded area is formed at a part of the flow channel-forming non-bonded area,
the first flexible substrate includes a through-hole that is in contact with the flow channel-forming non-bonded area,
shutter-forming non-bonded areas are formed on a bonding surface of the second flexible substrate and the third substrate in a band-like manner (e.g. two bands-like manner) at a near side and a far side of the through-hole relative to the mixing chamber-forming non-bonded area such that the shutter-forming non-bonded areas and the flow channel-forming non-bonded area intersect above and below via the second flexible substrate being interposed therebetween, at least one of both of the first flexible substrate and the second flexible substrate and the third substrate includes pressure supply ports that come through the substrate(s) so as to be in contact with the shutter-forming non-bonded areas,
a flow channel and a mixing chamber are formable by supplying pressure from the through-hole to raise a site above the flow channel-forming non-bonded area and a site above the mixing chamber-forming non-bonded area,
the flow channel is blockable by supplying pressure from the pressure supply ports to raise sites above the shutter-forming non-bonded areas, and
a target substance and a reagent are mixable in the mixing chamber by applying pressure to a top surface of the first flexible substrate above the mixing chamber to deform the mixing chamber.

The present invention also provides a third chip for analysis of a target substance, including:

a laminate, the laminate including:
a first flexible substrate;
a second flexible substrate; and
a third substrate, wherein
a flow channel-forming non-bonded area is formed on a bonding surface of the first flexible substrate and the second flexible substrate in a band-like manner,
the first flexible substrate includes a through-hole that is in contact with the flow channel-forming non-bonded area,
a first mixing chamber-forming non-bonded area and a second mixing chamber-forming non-bonded area each having a wider band width than the flow channel-forming non-bonded area are each formed on the bonding surface of the first flexible substrate and the second flexible substrate at a part of the flow channel-forming non-bonded area in this order from the through-hole side,
shutter-forming non-bonded areas are formed on a bonding surface of the second flexible substrate and the third substrate in a band-like manner (e.g. two bands-like manner) at a near side of the through-hole relative to the first mixing chamber-forming non-bonded area and a far side of the through-hole relative to the second mixing chamber-forming non-bonded area such that the shutter-forming non-bonded areas and the flow channel-forming non-bonded area intersect above and below via the second flexible substrate being interposed therebetween,
at least one of both of the first flexible substrate and the second flexible substrate and the third substrate includes pressure supply ports that come through the substrate(s) so as to be in contact with the shutter-forming non-bonded areas,
a flow channel, a first mixing chamber, and a second mixing chamber are formable by supplying pressure from the through-hole to raise a site above the flow channel-forming non-bonded area, a site above the first mixing chamber-forming non-bonded area, and a site above the second mixing chamber-forming non-bonded area,
the flow channel is blockable by supplying pressure from the pressure supply ports to raise sites above the shutter-forming non-bonded areas, and
a target substance and a reagent are mixable by moving them between the first mixing chamber and the second mixing chamber.

Effects of the Invention

According to the present invention, it is possible to provide a chip for analysis of a target substance that is compact and allows analysis of a target substance such as DNA with less time and effort.

BRIEF DESCRIPTION OF DRAWINGS

FIGS. 1(A)-1(C) show diagrams illustrating an example of the configuration of the first chip for analysis of a target substance of the present invention.

DESCRIPTION OF EXEMPLARY EMBODIMENT

The chip for analysis of a target substance of the present invention will be described with reference to exemplary embodiments. Note here that the present invention is not limited to these exemplary embodiments. Furthermore, the description for each Embodiment can be applied to another Embodiment unless otherwise indicated.

Embodiment 1

Figure 1A:
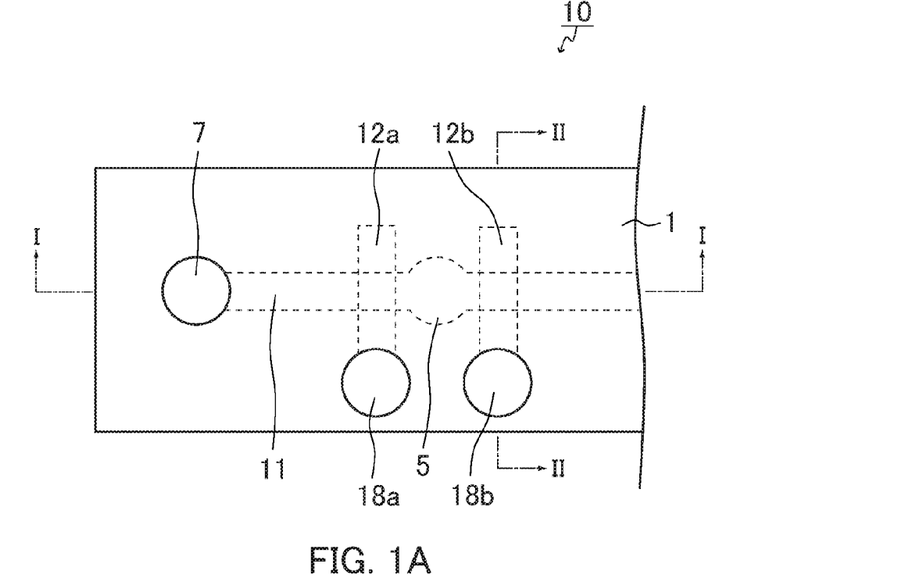
FIG. 1(A) is a schematic perspective plan view.
Figure 1B:
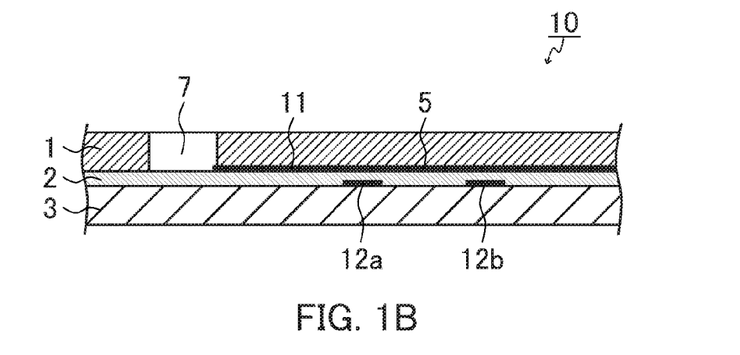
FIG. 1(B) is a schematic cross sectional view of FIG. 1(A) viewed from the line I-I.
Figure 1C:
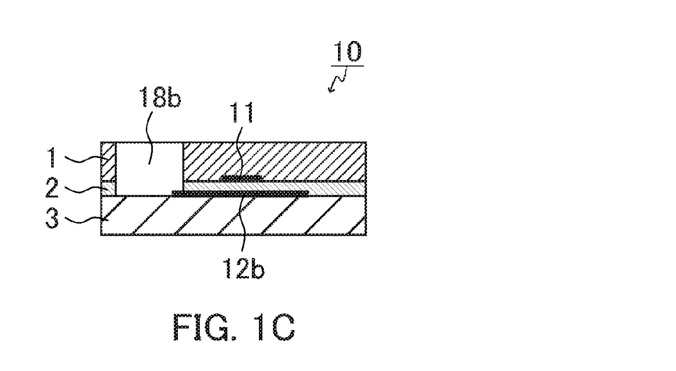
FIG. 1(C) is a schematic cross sectional view of FIG. 1(A) viewed from the line II-II.

FIGS. 1(A)-1(C) show an example of the configuration of the first chip for analysis of a target substance of the present invention. FIG. 1(A) is a schematic perspective plan view, FIG. 1(B) is a schematic cross sectional view of FIG. 1(A) viewed from the line I-I, and FIG. 1(C) is a schematic cross sectional view of FIG. 1(A) viewed from the line II-II. As shown in FIGS. 1(A)-1(C), a chip for analysis of a target substance 10 includes a laminate in which a first flexible substrate 1, a second flexible substrate 2, and a third substrate 3 are laminated. In the laminate, the laminate direction of substrates is referred to as the up-and-down direction (hereinafter, the same applies). A flow channel-forming non-bonded area 11 is formed on the bonding surface of the first flexible substrate 1 and the second flexible substrate 2 in a band-like manner and an extraction chamber-forming non-bonded area 5 having a wider band width than the flow channel-forming non-bonded area 11 is formed at a part of the flow channel-forming non-bonded area 11. The first flexible substrate 1 includes a through-hole 7 that is in contact with the flow channel-forming non-bonded area 11. Shutter-forming non-bonded areas 12a and 12b are formed on the bonding surface of the second flexible substrate 2 and the third substrate 3 in a band-like manner at the near side and the far side of the through-hole 7 relative to the extraction chamber-forming non-bonded area 5 such that the shutter-forming non-bonded areas 12a and 12b and the flow channel-forming non-bonded area 11 intersect above and below via the second flexible substrate 2 being interposed therebetween. The first flexible substrate 1 and the second flexible substrate 2 include pressure supply ports 18a and 18b that come through the substrates so as to be in contact with the shutter-forming non-bonded areas 12a and 12b respectively. It is also possible that the third substrate 3 includes the pressure supply ports 18a and 18b that come through the substrate so as to be in contact with the shutter-forming non-bonded areas 12a and 12b respectively. Although it is not shown in FIG. 1, a magnetic particle that binds to a target substance is placed above the extraction chamber-forming non-bonded area 5. In this Embodiment, the shutter-forming non-bonded area 12a and the pressure supply port 18a are optional components and are not indispensable, although the chip for analysis of a target substance of this Embodiment preferably includes these components.

In this Embodiment, the flow direction of liquid in the flow channel to be formed is along the flow channel-forming non-bonded area 11 and the through-hole 7 side is the upstream side. Therefore, it can be said that the shutter-forming non-bonded area 12a is formed at the downstream side of the through-hole 7 and the upstream side of the extraction chamber-forming non-bonded area 5, i.e., between the through-hole 7 and the extraction chamber-forming non-bonded area 5, and the shutter-forming non-bonded area 12b is formed at the downstream side of the extraction chamber-forming non-bonded area 5.

In FIGS. 1(A)-1(C), one through-hole 7 is provided at the left end of the flow channel-forming non-bonded area 11. However, the present invention is not limited thereto. An appropriate number of through-holes may be provided at any place as long as the through-hole is in contact with the flow channel-forming non-bonded area 11.

Furthermore, in FIGS. 1(A)-1(C), one pressure supply port 18a is provided at the end of the shutter-forming non-bonded area 12a and one pressure supply port 18b is provided at the end of the shutter-forming non-bonded area 12b. However, the present invention is not limited thereto. An appropriate number of pressure supply ports may be provided at any place as long as the pressure supply port is in contact with the shutter-forming non-bonded area.

There is no particular limitation on how the shutter-forming non-bonded areas 12a and 12b and the flow channel-forming non-bonded area 11 intersect as long as the shutter-forming non-bonded areas 12a and 12b and the flow channel-forming non-bonded area 11 intersect above and below via the second flexible substrate 2 being interposed therebetween. For example, although the shutter-forming non-bonded areas 12a and 12b and the flow channel-forming non-bonded area 11 intersect at right angles in FIGS. 1(A)-1(C), the present invention is not limited thereto.

The undersurface of the first flexible substrate 1 and the top surface of the second flexible substrate 2 are bonded with each other at around the flow channel-forming non-bonded area 11, through-hole 7, and the extraction chamber-forming non-bonded area 5. Preferably, the undersurface of the first flexible substrate 1 and the top surface of the second flexible substrate 2 are bonded with each other at an area excluding the flow channel-forming non-bonded area 11, the through-hole 7, and the extraction chamber-forming non-bonded area 5. Furthermore, the undersurface of the second flexible substrate 2 and the top surface of third substrate 3 are bonded with each other at an area excluding the shutter-forming non-bonded areas 12a and 12b and the pressure supply ports 18a and 18b.

The chip for analysis of a target substance 10 can be produced, for example, as follows. First, the first flexible substrate 1, the second flexible substrate 2, and the third substrate 3 are provided. Surface modification treatment for the purpose of increasing the bonding strength between the substrates may be applied to the undersurface of the first flexible substrate 1, the top surface and the undersurface of the second flexible substrate 2, and the top surface of the third substrate 3. Examples of the surface modification treatment include oxygen plasma treatment and excimer UV light irradiation treatment. The oxygen plasma treatment can be performed, for example, using a reactive ion etching (RIE) apparatus and the like in the presence of oxygen. The excimer UV light irradiation treatment can be performed, for example, using a dielectric barrier discharge lamp under an air atmosphere of atmospheric pressure.

Examples of the material of the first flexible substrate 1 include a silicone rubber such as polydimethylsiloxane (PDMS); a nitrile rubber; a hydrogenated nitrile rubber; a fluororubber; an ethylene-propylene rubber; a chloroprene rubber; an acrylic rubber; a butyl rubber; an urethane rubber; a chlorosulfonated polyethylene rubber; an epichlorohydrin rubber; a natural rubber; an isoprene rubber; a styrene-butadiene rubber; a butadiene rubber; a polysulfide rubber; a norbomene rubber; and a thermoplastic elastomer. These materials may be used alone or two or more of them may be used in combination. Among them, a silicone rubber such as PDMS is particularly preferable. The thickness of the first flexible substrate 1 is, for example, in the range from 10 µm to 5 mm in consideration of the strength thereof and the formation of the flow channel and the extraction chamber that will be described below.

There are no particular limitations on the methods of forming the through-hole 7 and the pressure supply ports 18a and 18b on the first flexible substrate 1, and conventionally known methods can be used. There are no particular limitations on the shapes of the through-hole 7 and the pressure supply ports 18a and 18b. The through-hole 7 and the pressure supply ports 18a and 18b can take any shape such as a cylinder shown in FIGS. 1(A)-1(C) and a prism, for example. The sizes of the through-hole 7 and the pressure supply ports 18a and 18b may be set appropriately, for example, according to the widths of the flow channel-forming non-bonded area and the shutter-forming non-bonded area that will be described below.

Examples of the material of the second flexible substrate 2 include those described for the first flexible substrate 1. While the material of the second flexible substrate 2 can be the same as or different from the material of the first flexible substrate, the material of the second flexible substrate 2 is preferably the same as the material of the first flexible substrate 1. Specifically, for example, in the case where the first flexible substrate 1 is silicone rubber, the second flexible substrate 2 is preferably silicone rubber. If the first flexible substrate 1 and the second flexible substrate 2 are both silicone rubber, the first flexible substrate 1 and the second flexible substrate 2 can be bonded by a self adsorption ability without using an adhesive agent. The thickness of the second flexible substrate 2 is, for example, in the range from 10 µm to 500 µm in consideration of the strength thereof and the blocking of the flow channel that will be described below.

There are no particular limitations on the methods of forming the pressure supply ports 18a and 18b on the second flexible substrate 2, and conventionally known methods can be used. The shapes and the sizes of the pressure supply ports 18a and 18b of the second flexible substrate 2 are, for example, the same as those of the pressure supply ports 18a and 18b of the first flexible substrate 1.

The flow channel-forming non-bonded area 11 is formed on the top surface of the second flexible substrate 2 in a band-like manner and the extraction chamber-forming non-bonded area 5 having a wider band width than the flow channel-forming non-bonded area 11 is formed at a part of the flow channel-forming non-bonded area 11. The flow channel-forming non-bonded area 11 and the extraction chamber-forming non-bonded area 5 each can be formed as, for example, an electrode film, a dielectric protective film, a semiconductor film, a fluorescent film, a superconductive film, a dielectric film, a solar cell film, an antireflection film, a wear-resistant film, an optical interference film, a reflection film, an antistatic film, a conductive film, an antifouling film, a hard coating film, a barrier film, an electromagnetic wave shielding film, an infrared shielding film, an ultraviolet absorbing film, a lubricating film, a shape memory film, a magnetic recording film, a light-emitting element film, a biocompatible film, a corrosion-resistant film, a catalyst film, or a gas sensor film, for example, by a conventionally known chemical thin film formation technology.

Specifically, for example, the aforementioned thin film can be formed by a plasma discharge treatment apparatus using an organic fluorine compound or a metal compound as reactive gas.

Examples of the organic fluorine compound include fluorocarbon compounds such as fluoromethane, fluoroethane, tetrafluoromethane, hexafluoromethane, 1,1,2,2-tetrafluoroethylene, 1,1,1,2,3,3-hexafluoropropane, hexafluoropropene, and 6-fluoropropylen; fluorohydrocarbon compounds such as 1,1-difluoroethylene, 1,1,1,2-tetrafluoroethane, and 1,1,2,2,3-pentafluoropropane; carbon fluorochloride compounds such as difluorodichloromethane and trifluorochloromethane; fluoroalcohols such as 1,1,1,3,3,3-hexafluoro-2-propanol, 1,3-difluoro-2-propanol, and perfluorobutanol; fluoro carboxylic ester such as vinyltrifluoroacetate and 1,1,1-trifluoroacetate; and fluoroketone such as acetyl fluoride, hexafluoro acetone, and 1,1,1-trifluoroacetone.

Examples of the metal compound include a single metal compound, a mixed metal compound, and an organic metal compound of Al, As, Au, B, Bi, Ca, Cd, Cr, Co, Cu, Fe, Ga, Ge, Hg, In, Li, Mg, Mn, Mo, Na, Ni, Pb, Pt, Rh, Sb, Se, Si, Sn, Ti, V, W, Y, Zn, and Zr.

The aforementioned thin film can be formed, for example, by a reactive ion etching system (RIE), a printing method, and the like in the presence of fluorocarbon ($CHF_3$) via a mask. As the printing method, for example, conventionally known printing methods such as roll printing, pattern printing, decalcomania, and electrostatic copying can be employed. In the case where the aforementioned thin film is formed by the printing method, for example, a metal fine particle, a conductive ink, an insulating ink, a carbon fine particle, a silane agent, parylene, a paint, a pigment, a dye, a water-based dye ink, a water-based pigment ink, an oil dye ink, an oil pigment ink, a solvent ink, a solid ink, a gel ink, a polymer ink, and the like can be used suitably for the material for forming the thin film. Examples of the metal fine particle include a single metal fine particle of, a mixed metal fine particle of two or more of, an oxide fine particle (for example, ITO fine particle or the like) of the single metal or the mixed metal of, and an organic metal compound fine particle of Al, As, Au, B, Bi, Ca, Cd, Cr, Co, Cu, Fe, Ga, Ge, Hg, In, Li, Mg, Mn, Mo, Na, Ni, Pb, Pt, Rh, Sb, Se, Si, Sn, Ti, V, W, Y, Zn, and Zr.

The thickness of each of the flow channel-forming non-bonded area 11 and the extraction chamber-forming non-bonded area 5 is, for example, in the range from 10 nm to 10 μm and preferably in the range from 50 nm to 3 μm in consideration of uniform formation of the flow channel-forming non-bonded area 11 and the extraction chamber-forming non-bonded area 5 and the bonding ability between the first flexible substrate 1 and the second flexible substrate 2 at an area excluding the non-bonded area. The width of the flow channel-forming non-bonded area 11 is, for example, in the range from 10 μm to 3000 μm in consideration of the formation of the flow channel that will be described below, a supply amount of each of a reagent and a target substance such as DNA, and the like. The size of the extraction chamber-forming non-bonded area 5 is, for example, in the range from 3 $mm^2$ to 300 $mm^2$ and preferably in the range from 16 $mm^2$ to 50 $mm^2$ in consideration of the formation of the extraction chamber that will be described below, a supply amount of each of a reagent and a target substance such as DNA, and the like.

The shape of the flow channel-forming non-bonded area 11 is not limited to a linear band shown in FIGS. 1(A)-1(C), and, for example, various shaped bands such as a Y-shaped band and an L-shaped band can be employed. The shape of the extraction chamber-forming non-bonded area 5 is also not limited to a circle shown in FIGS. 1(A)-1(C), and, for example, any shape such as a rectangle can be employed.

Examples of the material of the third substrate 3 include acryl, a silicone rubber such as PDMS, glass, polyethylene terephthalate, polyethylene naphthalate, polyethylene, polypropylene, cellophane, cellulose diacetate, cellulose acetate butyrate, cellulose acetate propionate, cellulose acetate phthalate, cellulose triacetate, cellulose nitrate, polyvinylidene chloride, polyvinyl alcohol, ethylene vinyl alcohol, polycarbonate, a norbomene resin, polymethylpentene, polyether ketone, polyimide, polyethersulfone, polyether ketone imide, polyamide, a fluororesin, nylon, polymethyl methacrylate, polyarylate, a polylactic resin, polybutylene succinate, a nitrile rubber, a hydrogenated nitrile rubber, a fluororubber, an ethylene-propylene rubber, a chloroprene rubber, an acrylic rubber, a butyl rubber, an urethane rubber, a chlorosulfonated polyethylene rubber, an epichlorohydrin rubber, a natural rubber, an isoprene rubber, a styrene-butadiene rubber, a butadiene rubber, a polysulfide rubber, a norbomene rubber, and thermoplastic elastomer. These materials may be used alone or two or more of them may be used in combination. Among them, acryl is particularly preferable. The thickness of the third substrate 3 is, for example, in the range from 300 μm to 10 mm in consideration of strength and economic efficiency.

Preferably, surface treatment using a surface treatment agent is applied to the top surface of the third substrate 3 for the purpose of increasing the bonding ability between the top surface of the third substrate 3 and the undersurface of the second flexible substrate 2 at an area excluding the non-bonded area. Examples of the surface treatment agent include alkylsilane such as dimethylsilane, tetramethylsilane, and tetraethylsilane; organic silicon compounds of silicon alkoxysilane such as tetramethoxysilane, tetraethoxysilane, tetrapropoxysilane, dimethyldiethoxysilane, methyltrimethoxysilane, and ethyltriethoxysilane; silicon-hydrogen compounds such as monosilane and disilane; halogenated silicon compounds such as dichlorosilane, trichlorosilane, and tetrachlorosilane; silazane such as hexamethyldisilazane; and silicon compounds into which functional groups are introduced such as vinyl, epoxy, styryl, methacryloxy, acryloxy, amino, ureide, chloropropyl, mercapto, sulfide, and isocyanate.

Shutter-forming non-bonded areas 12a and 12b are formed on the top surface of the third substrate 3 in a band-like manner. The shutter-forming non-bonded areas 12a and 12b may be formed, for example, using the same material as those used for the flow channel-forming non-bonded area 11 and the extraction chamber-forming non-bonded area 5 such that the shutter-forming non-bonded areas 12a and 12b have the same thickness as the flow channel-forming non-bonded area 11 and the extraction chamber-forming non-bonded area 5. The width of each of the shutter-forming non-bonded areas 12a and 12b is, for example, in the range from 10 μm to 5000 μm in consideration of the blocking of the flow channel that will be described below and economic efficiency.

Next, the first flexible substrate 1, the second flexible substrate 2, and the third substrate 3 are laminated. At this time, although it is not shown, a magnetic particle that binds to a target substance such as DNA is placed above the extraction chamber-forming non-bonded area 5. "Bonding" may be, for example, direct or indirect bonding of the target substance to the magnetic particle. In the former case, an example of the direct bonding includes adhesion of the target substance to the magnetic particle itself. In the latter case, examples of the indirect bonding include adsorption or adhesion of the target substance to a predetermined substance to which a magnetic particle coating is applied and bonding of the target substance to the magnetic particle by reaction using a reactive substance.

Preferably, the magnetic particle is, for example, a sphere and the particle size is, for example, in the range from 0.3 μm to 5 μm. As the magnetic particle, for example, a substance having a porous surface or a substance in which at least one of silica gel and cellulose is mixed is suitable.

In this manner, the chip for analysis of a target substance 10 shown in FIGS. 1(A)-(C) can be obtained.

Next, the first target substance analysis method of the present invention can be performed using the first chip for analysis of a target substance of the present invention. The first target substance analysis method is characterized, for example, by using the first chip for analysis of a target substance of the present invention and including the following steps (a1) to (d1):

(a1) a step of forming a shutter portion for blocking the flow channel by supplying pressure from the pressure supply port to raise a site above the shutter-forming non-bonded area;

(b1) a step of forming the flow channel and extraction chamber by supplying pressure from the through-hole to raise a site above the flow channel-forming non-bonded area and a site above the extraction chamber-forming non-bonded area;

(c1) a step of injecting an analysis sample into the flow channel and the extraction chamber; and (d1) a step of capturing the target substance in the analysis sample that is bound to the magnetic particle by generating a magnetic field at at least one of the undersurface of the third substrate directly below the end of the extraction chamber at the opposite side of the through-hole and the top surface of the first flexible substrate directly above the end of the extraction chamber at the opposite side of the through-hole.

In the first target substance analysis method of the present invention, there is no particular limitation on the order of the above steps. For example, the steps may be performed in the order from step (a1) to step (d1). The shutter portion formation step (a1) and the flow channel and extraction chamber formation step (b1) may be performed simultaneously or either of the steps (a1) and (b1) may be performed in advance, for example. Furthermore, the analysis sample injection step (c1) may be performed simultaneously with the flow channel and extraction chamber formation step (b1), for example As the first target substance analysis method of the present invention, an example of the usage of the chip for analysis of a target substance 10 shown in FIGS. 1(A)-1(C) will be described with reference to FIG. 2. The aspect shown in FIG. 2 is an example and the present invention is not limited to this aspect.

Figure 2:
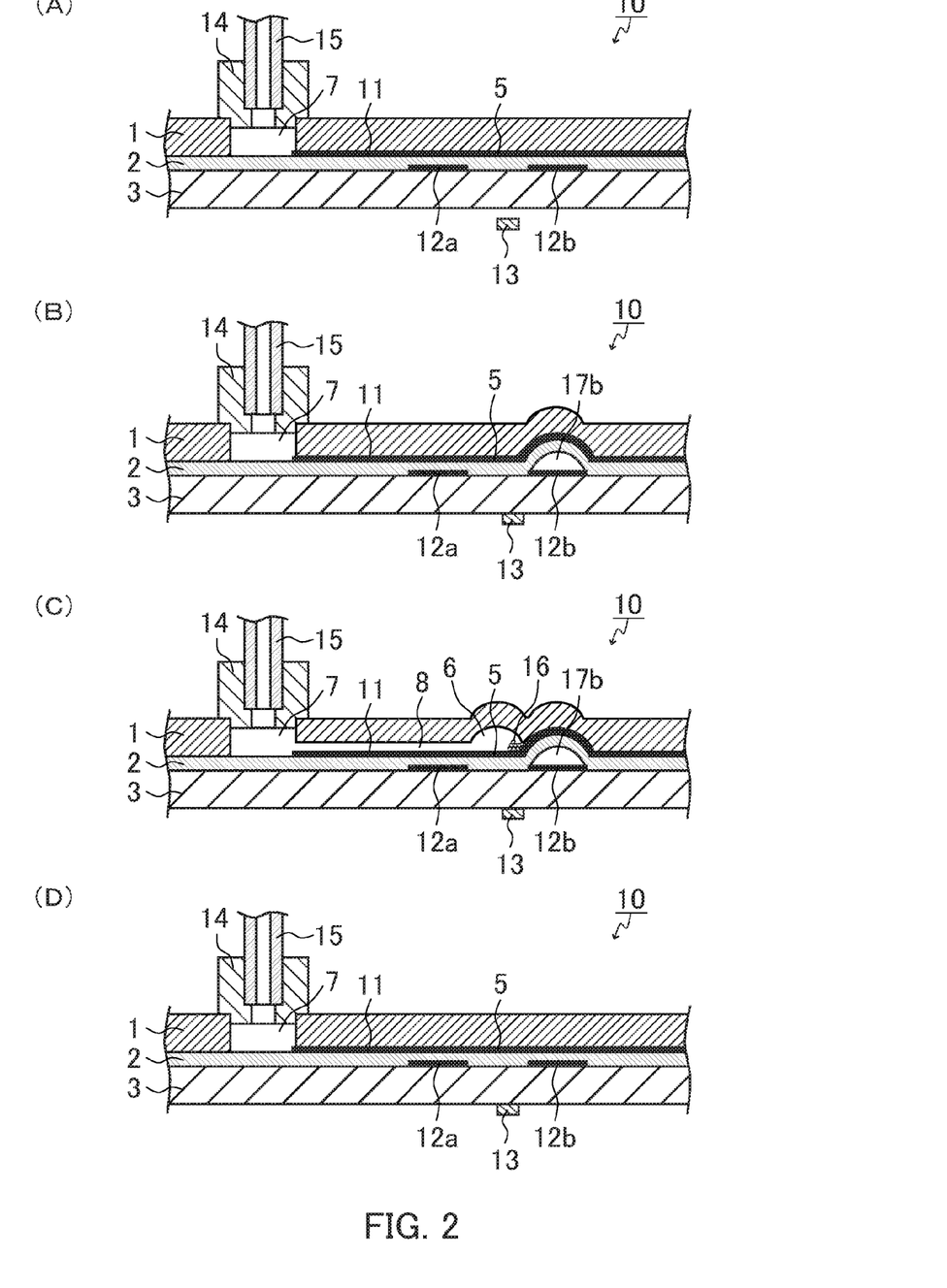
FIG. 2 shows schematic cross sectional views illustrating an example of the usage of the chip for analysis of a target substance shown in FIGS. 1(A)-1(C).

First, as shown in FIG. 2(A), an adapter 14 is provided at the opening portion of the through-hole 7 serving as an introduction portion of liquid or gas, and an injection tube 15 is connected to the adapter 14. The shape of the adapter 14 is not limited to that shown in FIG. 2(A). For example, the adapter 14 may not be in the form of partially inserted in the through-hole 7 but may be in the form of directly fixed to the top surface of the first flexible substrate 1. Furthermore, the injection tube 15 may be directly connected to the through-hole 7 without using the adapter 14. As the material for the adapter 14, although a silicone rubber such as PDMS is preferable, any other material can be used. In the case where a material other than PDMS is used, an appropriate adhesive agent may be used for fixing the adapter 14 to the top surface of the first flexible substrate 1. An example of the injection tube 15 includes a Teflon (registered trademark) tube. One end of the injection tube 15 is fixed to the adapter 14 using an appropriate adhesive agent. The other end of the injection tube 15 is connected to an appropriate undiluted solution supply means, an appropriate pressure application means (for example, a micro-pump, a syringe, or the like), and the like although it is not shown.

The adapter 14 to which the injection tube 15 is connected is provided also at each of the pressure supply ports 18a and 18b although it is not shown. Then, gas is injected at high pressure from the injection tube 15 via the pressure supply port 18b. Thereby, as shown in FIG. 2(B), a site above the shutter-forming non-bonded area 12b is raised to form the shutter-forming void 17b. Specifically, only a part of the first flexible substrate 1 and a part of the second flexible substrate 2 positioned above the shutter-forming non-bonded area 12b are raised from the top surface of the third substrate 3 to form the shutter-forming void 17b. The shutter-forming void 17b formed by raising is also referred to as a shutter portion (hereinafter, the same applies). The gas is, for example, air or the like, and the level of high pressure is, for example, in the range from 10 kPa to 300 kPa (hereinafter, the same applies).

Next, a liquid analysis sample to be analyzed is injected into the chip for analysis of a target substance 10. In the present invention, there is no particular limitation on the type of the analysis sample, and, for example, the type of the analysis sample can be selected appropriately according to the type of the target substance. Examples of the target substance include cells and intracellular components, and specific examples thereof include nucleic acids such as DNA and RNA. In the case where the target substance is the intracellular component such as the nucleic acids, the analysis sample may be, for example, a sample in which a target substance is eluted from a cell, i.e., an elution sample of a cell (also referred to as a target substance-eluted sample), or a sample in which a target substance is not eluted from a cell, i.e., a sample that contains a cell. In the latter case, for example, the target substance such as the nucleic acid or the like may be eluted from a cell in the analysis sample in the chip for analysis of a target substance 10.

Specifically, gas is injected at high pressure from the injection tube 15 after injecting the analysis sample into the through-hole 7 or the analysis sample is injected into the through-hole 7 with application of positive pressure. Thereby, as shown in FIG. 2(B), a site above the flow channel-forming non-bonded area 11 and a site above the extraction chamber-forming non-bonded area 5 are raised and the flow channel 8 and the extraction chamber 6 are formed. Specifically, only parts of the first flexible substrate 1 positioned above the flow channel-forming non-bonded area 11 and the extraction chamber-forming non-bonded area 5 are raised from the top surface of the second flexible substrate 2 to form the flow channel 8 and extraction chamber 6. On this occasion, a site above the flow channel-forming non-bonded area 11 positioned further ahead of the shutter-forming void 17b, i.e., a site above the flow channel-forming non-bonded area 11 positioned at the downstream side of the shutter-forming void 17b is blocked by the shutter-forming void 17b, and therefore the flow channel is not formed. At this time, in the extraction chamber 6, the target substance contained in the analysis sample that has been injected binds to the magnetic particle 16.

In the case where the analysis sample is the sample that contains a cell as described above, for example, an elution reagent that causes a target substance such as a nucleic acid to be eluted from the cell may be injected into the chip for analysis of a target substance 10 before, at the same time as, or after the injection of the analysis sample. The method of injection is, for example, the same as that described for the analysis sample. Then, the target substance eluted from the cell by the elution reagent binds to the magnetic particle 16 in the extraction chamber 6. It is also possible to preliminarily place the elution reagent, for example, at the extraction chamber-forming non-bonded area 5 or at the flow channel-forming non-bonded area 11 between the through-hole 7 and the extraction chamber-forming non-bonded area 5.

Next, a washing reagent is injected into the chip for analysis of a target substance 10. There is no particular limitation on the method of injection of the washing reagent, and, for example, the washing reagent is injected from the injection tube 15 via the through-hole 7 in the same manner as the analysis sample.

Thereafter, a magnetic field is generated at the undersurface of the third substrate 3. Specifically, a magnetic field is generated at the undersurface of the third substrate 3 directly below the end of the extraction chamber 6 at the opposite side of the through-hole 7. Thereby, in the extraction chamber 6, a target substance such as DNA that is bound to the magnetic particle 16 is captured. In this manner, by generating a magnetic field at the undersurface of the third substrate 3, the leak of the magnetic particle 16 to the flow channel 8 further ahead of the extraction chamber 6 can be prevented even in the case where the flow channel 8 is formed at the downstream side of the extraction chamber 6. The magnetic field may be generated, for example, at the top surface side of the first flexible substrate 1. Specifically, the magnetic field may be generated at the top surface side of the first flexible substrate 1 directly above the end of the extraction chamber 6 at the opposite side of the through-hole 7.

There is no particular limitation on the method of generating a magnetic field, and an example thereof includes a method of making the chip for analysis of a target substance 10 into contact with a magnet 13 such as an electromagnet or a permanent magnet such as an alnico magnet, a ferrite magnet, a neodymium magnet, or a samarium-cobalt magnet.

Next, the pressure of the gas injecting from the through-hole 7 and the pressure supply port 18*b* is set about atmospheric pressure. Thereby, as shown in FIG. 2(C), the shutter-forming void 17*b* and the voids of the flow channel 8 and the extraction chamber 6 are vanished. Thereafter, gas is injected at high pressure from the injection tube 15 via the through-hole 7. Thereby, substances excluding the target substance that is bound to the magnetic particle 16, e.g., the washing reagent and the like can be discharged from the flow channel 8. In this manner, the chip for analysis of a target substance of this Embodiment allows extraction of a target substance such as DNA from the analysis sample efficiently by the magnetic particle 16. Since extraction of the target substance can be also referred to as separation of the target substance from the analysis sample, the extraction chamber can be also referred to as, for example, a separation chamber of the target substance.

Embodiment 2

Figure 3:
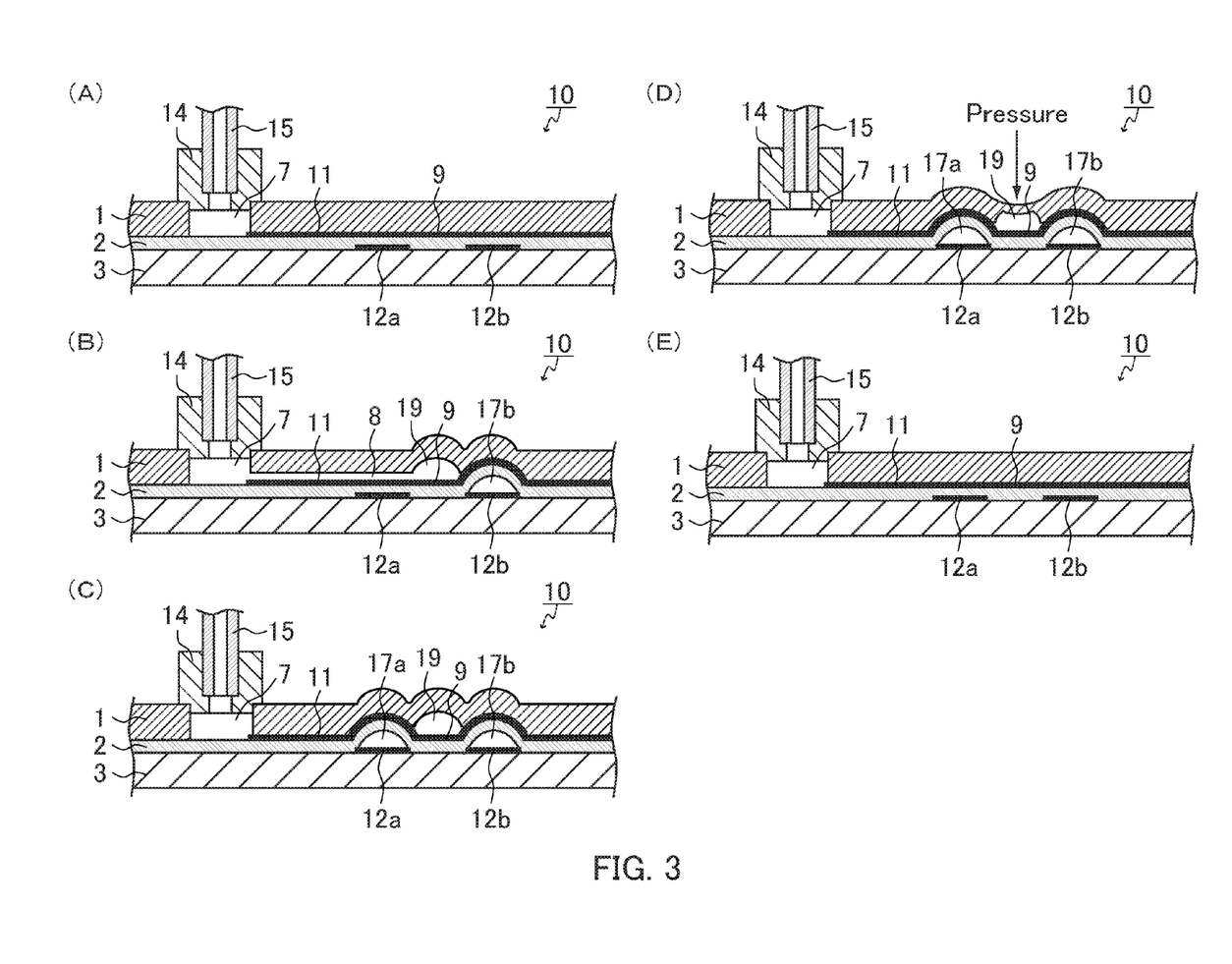
FIG. 3 shows schematic cross sectional views illustrating an example of the configuration of the second chip for analysis of a target substance of the present invention.

FIG. 3 shows an example of the configuration of the second chip for analysis of a target substance of the present invention. The aspect shown in FIG. 3 is an example and the present invention is not limited to this aspect. In FIG. 3, identical parts to those shown in FIGS. 1 and 2 are indicated with identical numerals and symbols. The chip for analysis of a target substance 10 shown in FIG. 3 has the configuration identical to that of the chip for analysis of a target substance 10 shown in FIGS. 1(A)-1(C) and 2 except that the extraction chamber-forming non-bonded area 5 has the function of a mixing chamber-forming non-bonded area 9 and does not contain the magnetic particle 16.

In the analysis of the target substance, for example, various reagents are used. The chip for analysis of a target substance of this Embodiment allows mixing of the reagent and the analysis sample or the target substance in the analysis sample in the mixing chamber 19 in the manner described below. There is no particular limitation on the reagent, and can be selected appropriately according to, for example, the type of the analysis sample, the type of the target substance, and the analysis method. Specific examples of the reagent include the aforementioned elution reagent that causes a target substance to be eluted from the cell, a reaction reagent that reacts with the target substance, and the washing reagent.

Next, the second target substance analysis method of the present invention can be performed using the second chip for analysis of a target substance of the present invention. The second target substance analysis method is characterized, for example, by using the second chip for analysis of a target substance of the present invention and including the following steps (a2) to (f2):

(a2) a step of forming a shutter portion for blocking the flow channel by supplying pressure from the pressure supply port to raise a site above the shutter-forming non-bonded area at the far side of the through-hole relative to the mixing chamber-forming non-bonded area;

(b2) a step of forming the flow channel and the mixing chamber by supplying pressure from the through-hole to raise a site above the flow channel-forming non-bonded area and a site above the mixing chamber-forming non-bonded area;

(c2) a step of injecting an analysis sample into the flow channel and the mixing chamber;

(d2) a step of injecting a reagent into the flow channel and the mixing chamber;

(e2) a step of forming a shutter portion for blocking the flow channel by supplying pressure from the pressure supply port to raise a site above the shutter-forming non-bonded area at the near side of the through-hole relative to the mixing chamber-forming non-bonded area; and (f2) a step of mixing the target substance in the analysis sample and the reagent in the mixing chamber by applying pressure to the top surface of the first flexible substrate above the mixing chamber to deform the mixing chamber.

In the second target substance analysis method of the present invention, there is no particular limitation on the order of the above steps. For example, the steps may be performed in the order from step (a2) to step (f2). The shutter portion formation step (a2) and the flow channel and mixing chamber formation step (b2) may be performed simultaneously or either of the steps (a2) and (b2) may be performed in advance, for example. The analysis sample injection step (c2) and the reagent injection step (d2) may be performed simultaneously or either of the steps (c2) and (d2) may be performed in advance, for example. Furthermore, the analysis sample injection step (c2) and the reagent injection step (d2) may be performed simultaneously with the flow channel and mixing chamber formation step (b2), for example.

As the second target substance analysis method of the present invention, an example of the usage of the chip for analysis of a target substance 10 will be described with reference to FIG. 3. First, as shown in FIGS. 3(A) and 3(B), the steps to the analysis sample injection step (steps before washing reagent injection) are performed in the same manner as in Embodiment 1. At this time, the extraction chamber 6 is formed in Embodiment 1 whereas the mixing chamber 19 is formed in this Embodiment.

Note here that the aforementioned various reagents may be injected into the chip for analysis of a target substance 10, for example, before, at the same time as, or after the injection of the analysis sample. The method of injection is, for example, the same as that described for the analysis sample. In the case where the analysis sample is the sample that contains a cell as described above, for example, the elution reagent, the reaction reagent that reacts with the eluted target substance, the washing reagent that washes the target substance, and the like may be injected as the reagent. Furthermore, in the case where the analysis sample is the target substance-eluted sample as described above, for example, the reaction reagent, the washing reagent, and the like may be injected as the reagent. It is also possible to preliminarily place the elution reagent and the reaction reagent, for example, at the mixing chamber-forming non-bonded area 9 or at the flow channel-forming non-bonded area 11 between the through-hole 7 and the mixing chamber-forming non-bonded area 9.

Next, gas is injected at high pressure from the injection tube 15 via the pressure supply port 18a. Thereby, as shown in FIG. 3(C), a site above the shutter-forming non-bonded area 12a is raised to form the shutter-forming void 17a. Specifically, only a part of the first flexible substrate 1 and a part of the second flexible substrate 2 positioned above the shutter-forming non-bonded area 12a are raised from the top surface of the third substrate 3 to form the shutter-forming void 17a. The gas is, for example, air or the like, and the level of high pressure is, for example, in the range from 10 kPa to 300 kPa (hereinafter, the same applies). Next, the pressure of the gas injecting from the through-hole 7 is set about atmospheric pressure. Thereby, as shown in FIG. 3(C), the void of the flow channel 8 at the upstream side of the shutter-forming void 17a is vanished.

Next, as shown in FIG. 3(D), the mixing chamber 19 is deformed by applying pressure to the top surface of the first flexible substrate 1 above the mixing chamber 19. Thereby, the target substance and the reagent are mixed in the mixing chamber 19. There is no particular limitation on the method of applying pressure to the position above the mixing chamber 19, and, for example, gas may be sprayed at high pressure or an object may be pressed.

Next, the pressure of the gas injecting from the pressure supply ports 18a and 18b is set about atmospheric pressure. Thereby, as shown in FIG. 3(E), the shutter-forming voids 17a and 17b and the void of the mixing chamber 19 are vanished. Thereafter, gas is injected at high pressure from the injection tube 15 via the through-hole 7. Thereby, the target substance mixed with the reagent can be forwarded to the next step.

In the chip for analysis of a target substance of this Embodiment, the same magnetic particle as described in Embodiment 1 may be placed at the mixing chamber-forming non-bonded area 9. In this case, the mixing chamber 19 also has the function of an extraction chamber.

Embodiment 3

In the third chip for analysis of a target substance of the present invention, as described above, two shutter-forming non-bonded areas are formed on the bonding surface of the second flexible substrate and the third substrate at the near side of the through-hole relative to the first mixing chamber-forming non-bonded area and at the far side of the through-hole relative to the second mixing chamber-forming non-bonded area. In the third chip for analysis of a target substance, for example, the third shutter-forming non-bonded area may be further formed on the bonding surface of the second flexible substrate and the third substrate in a band-like manner such that the third shutter-forming non-bonded area and the flow channel-forming non-bonded area intersect above and below via the second flexible substrate being interposed therebetween. This shutter-forming non-bonded area may be formed at the far side of the through-hole relative to the first mixing chamber-forming non-bonded area, for example. In this case, the flow channel at the upstream side and the downstream side of the first mixing chamber can be blocked respectively by the shutter portions.

Figure 4:
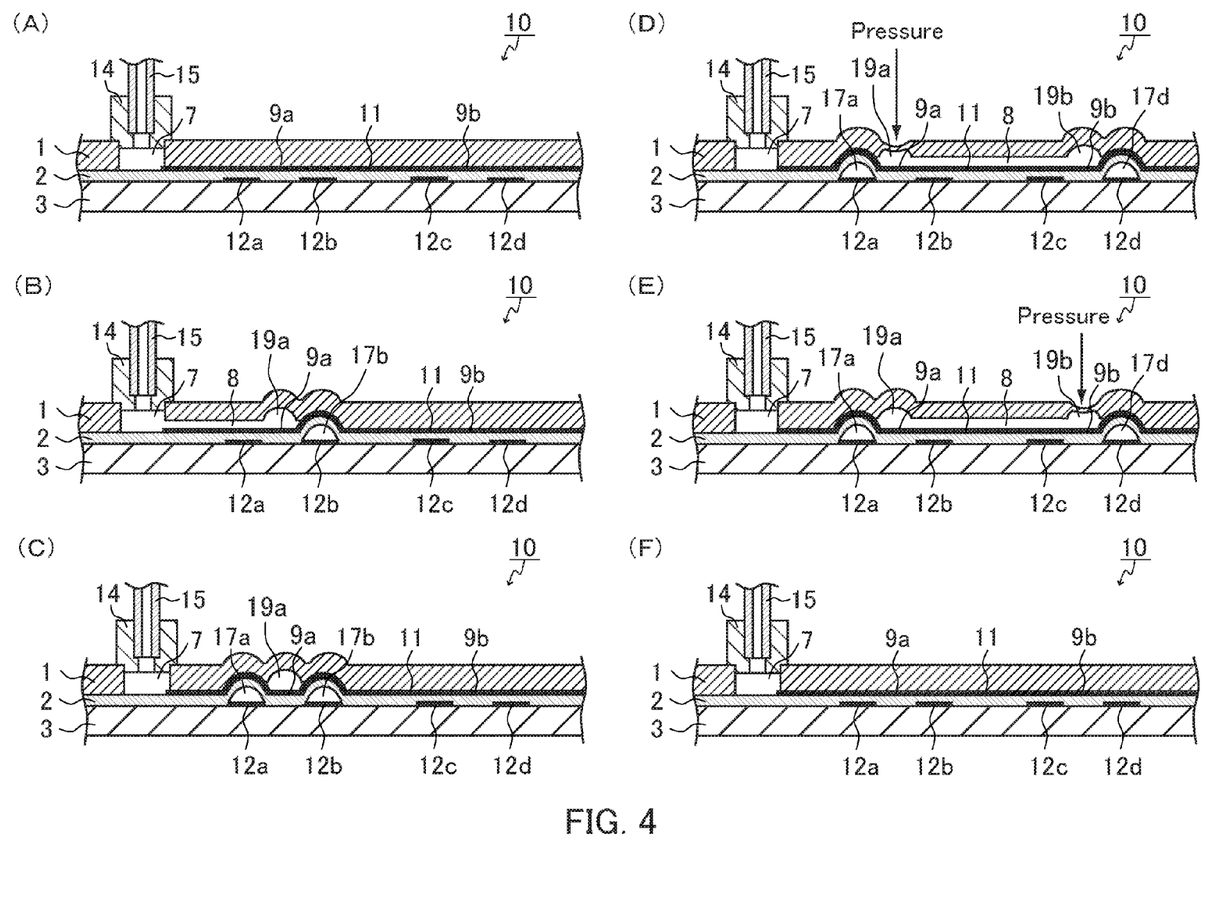
FIG. 4 shows schematic cross sectional views illustrating an example of the configuration of the third chip for analysis of a target substance of the present invention.

FIG. 4 shows an example of the configuration of the third chip for analysis of a target substance of the present invention. The aspect shown in FIG. 4 is an example and the present invention is not limited to this aspect. In FIG. 4, identical parts to those shown in FIGS. 1(A)-(C) to 3 are indicated with identical numerals and symbols. The chip for analysis of a target substance 10 shown in FIG. 4 has the configuration identical to that of the chip for analysis of a target substance shown in FIG. 3 except that the chip for analysis of a target substance 10 shown in FIG. 4 includes two mixing chamber-forming non-bonded areas (9a and 9b), four shutter-forming non-bonded areas (12a to 12d), and four pressure supply ports. Although it is not shown, four pressure supply ports are referred to as pressure supply ports 18a to 18d for convenience sake.

Although it is not shown, the shutter-forming non-bonded areas 12c and 12d are respectively in contact with the pressure supply ports 18c and 18d that come through the first flexible substrate 1 and the second flexible substrate 2 as in the case of the shutter-forming non-bonded areas 12a and 12b shown in FIG. 1(A). The pressure supply ports 18c and 18d may be formed on the third substrate 3 in such a manner that they come through the third substrate 3 so as to be in contact with the shutter-forming non-bonded areas 12c and 12d. In this Embodiment, the shutter-forming non-bonded areas 12b and 12c and the pressure supply ports 18b and 18c are optional components and are not indispensable, although the chip for analysis of a target substance of this Embodiment preferably includes these components. Furthermore, in this Embodiment, the shutter-forming non-bonded areas 12b and 12c and the pressure supply ports 18b and 18c may be respectively formed as one component, and the number of the non-bonded areas and the pressure supply ports may be respectively three.

Next, the third target substance analysis method of the present invention can be performed using the third chip for analysis of a target substance of the present invention. The third target substance analysis method is characterized, for example, by using the third chip for analysis of a target substance of the present invention and including the following steps (a3) to (f3):

(a3) a step of forming the flow channel, the first mixing chamber, and the second mixing chamber by supplying pressure from the through-hole to raise a site above the flow channel-forming non-bonded area, a site above the first mixing chamber-forming non-bonded area, and a site above the second mixing chamber-forming non-bonded area;

(b3) a step of injecting an analysis sample into the flow channel and the mixing chamber;

(c3) a step of injecting a reagent into the flow channel and the mixing chamber;

(d3) a step of forming a shutter portion for blocking the flow channel by supplying pressure from the pressure supply port to raise a site above the shutter-forming non-bonded area at the near side of the through-hole relative to the first mixing chamber-forming non-bonded area;

(e3) a step of forming a shutter portion for blocking the flow channel by supplying pressure from the pressure supply port to raise a site above the shutter-forming non-bonded area at the far side of the through-hole relative to the second mixing chamber-forming non-bonded area; and (f3) a step of mixing the target substance in the analysis sample and the reagent by moving them between the first mixing chamber and the second mixing chamber.

In the third target substance analysis method of the present invention, there is no particular limitation on the order of the above steps. For example, the steps may be performed in the order from step (a3) to step (f3). The step (d3) may be performed, for example, before, at the same time as, or after the step (a3) and is preferably performed before the steps (b3) and (c3). The step (e3) is preferably performed, for example, after the steps (b3) and (c3).

Furthermore, in the present invention, the formation of the first mixing chamber and the second mixing chamber in the step (a3) may be performed, for example, as a separated step. In this case, the step (a3) may be the steps (a3-1) and (a3-2) described below:

(a3-1) a step of forming the flow channel and the first mixing chamber by supplying pressure from the through-hole to raise a site above the flow channel-forming non-bonded area between the through-hole and the first mixing chamber-forming non-bonded area and a site above the first mixing chamber-forming non-bonded area; and (a3-2) a step of forming the flow channel and the second mixing chamber by applying pressure to a site above the first mixing chamber to deform the first mixing chamber so as to raise a site above the flow channel-forming non-bonded area between the first mixing chamber-forming non-bonded area and the second mixing chamber-forming non-bonded and a site above the second mixing chamber-forming non-bonded area.

The first mixing chamber formation step (a3-1) is preferably performed before or at the same time as the analysis sample injection step (b3) and the reagent injection step (c3). The second mixing chamber formation step (a3-2) may be performed, for example, before, after, or during the shutter portion formation steps (d3) and (e3).

Furthermore, in the case where the third chip for analysis of a target substance includes the third shutter-forming non-bonded area, in advance of the first mixing chamber formation step (a3-1) or in advance of the analysis sample injection step (b3) and the reagent injection step (c3), a shutter portion may be formed by raising a site above the third shutter-forming non-bonded area.

The chip for analysis of a target substance 10 shown in FIG. 4 is used, for example, as follows. First, as shown in FIG. 4(A), in the same manner as in Embodiment 1, the adapter 14 to which the injection tube 15 is connected is provided at each of the through-hole 7 and the pressure supply ports 18a to 18d.

Next, gas is injected at high pressure from the injection tube 15 via the pressure supply port 18b. Thereby, as shown in FIG. 4(B), a site above the shutter-forming non-bonded area 12b is raised to form the shutter-forming void 17b. Specifically, only a part of the first flexible substrate 1 and a part of the second flexible substrate 2 positioned above the shutter-forming non-bonded area 12b are raised from the top surface of the third substrate 3 to form the shutter-forming void 17b. The gas is, for example, air or the like, and the level of high pressure is, for example, in the range from 10 kPa to 300 kPa (hereinafter, the same applies).

Next, gas is injected at high pressure from the injection tube 15 after injecting the analysis sample into the through-hole 7 or the analysis sample is injected into the through-hole 7 with application of positive pressure. Thereby, as shown in FIG. 4(B), a site above the flow channel-forming non-bonded area 11 and a site above the first mixing chamber-forming non-bonded area 9a are raised and the flow channel 8 and the first mixing chamber 19a are formed. Specifically, only parts of the first flexible substrate 1 positioned above the flow channel-forming non-bonded area 11 and the first mixing chamber-forming non-bonded area 9a are raised from the top surface of the second flexible substrate 2 to form the flow channel 8 and the first mixing chamber 19a. On this occasion, a site above the flow channel-forming non-bonded area 11 positioned further ahead of the shutter-forming void 17b, i.e., a site above the flow channel-forming non-bonded area 11 positioned at the downstream side of the shutter-forming void 17b is blocked by the shutter-forming void 17b, and therefore the flow channel is not formed. At this time, in the same manner as in Examples 1 and 2, for example, the reagent is injected into the chip for analysis of a target substance 10. In the case where the analysis sample is the sample that contains a cell as described above and the elution reagent is used as the reagent, a target substance such as DNA is eluted from the cell in the first mixing chamber 19a.

Next, gas is injected at high pressure from the injection tube 15 via the pressure supply port 18a. Thereby, as shown in FIG. 4(C), a site above the shutter-forming non-bonded area 12a is raised to form the shutter-forming void 17a. Specifically, only a part of the first flexible substrate 1 and a part of the second flexible substrate 2 positioned above the shutter-forming non-bonded area 12a are raised from the top surface of the third substrate 3 to form the shutter-forming void 17a. The gas is, for example, air or the like, and the level of high pressure is, for example, in the range from 10 kPa to 300 kPa (hereinafter, the same applies). Next, the pressure of the gas injecting from the through-hole 7 is set about atmospheric pressure. Thereby, as shown in FIG. 4(C), the void of the flow channel 8 at the upstream side of the shutter-forming void 17a is vanished.

Next, the pressure of the gas injecting from the pressure supply port 18b is set about atmospheric pressure. Thereby, as shown in FIG. 4(D), the void of the shutter-forming void 17b is vanished. Thereafter, gas is injected at high pressure from the injection tube 15 via the pressure supply port 18d. Thereby, as shown in FIG. 4(D), a site above the shutter-forming non-bonded area 12d is raised to form the shutter-forming void 17d. Specifically, only a part of the first flexible substrate 1 and a part of the second flexible substrate 2 positioned above the shutter-forming non-bonded area 12d are raised from the top surface of the third substrate 3 to form the shutter-forming void 17d.

Then, pressure is applied to the top surface of the first flexible substrate 1 above the first mixing chamber 19a.

Thereby, a part of the first flexible substrate 1 positioned above the flow channel-forming non-bonded area 11 between the first mixing chamber-forming non-bonded area 9*a* and the second mixing chamber-forming non-bonded area 9*b* and a part of the first flexible substrate 1 positioned above the second mixing chamber-forming non-bonded area 9*b* are raised from the top surface of the second flexible substrate 2 to form the flow channel 8 and the second mixing chamber 19*b*. Thereby, the target substance and the reagent are moved from the first mixing chamber 19*a* to the second mixing chamber 19*b*.

Next, as shown in FIG. 4(E), pressure is applied to the top surface of the first flexible substrate 1 above the second mixing chamber 19*b*. Thereby, the target substance and the reagent are moved from the second mixing chamber 19*b* to the first mixing chamber 19*a*.

Thereafter, pressure is alternately applied to the top surface of the first flexible substrate 1 positioned above the first mixing chamber 19*a* and the top surface of the first flexible substrate 1 positioned above the second mixing chamber 19*b* to alternately deform the first mixing chamber 19*a* and the second mixing chamber 19*b*. Thereby, the target substance and the reagent are mixed by moving between the first mixing chamber 19*a* and the second mixing chamber 19*b*. There is no particular limitation on the method of applying pressure to a site above the first mixing chamber 19*a* and a site above the second mixing chamber 19*b*, and, for example, gas may be sprayed at high pressure or an object may be pressed.

Furthermore, the method of mixing the target substance and the reagent by moving them between the first mixing chamber 19*a* and the second mixing chamber 19*b* is not limited to the method of alternately applying pressure to a site above the first mixing chamber 19*a* and a site above the second mixing chamber 19*b* to alternately deform the first mixing chamber 19*a* and the second mixing chamber 19*b*, and any method can be employed. For example, the target substance and the reagent may be mixed by applying air pressure between the first mixing chamber 19*a* and the second mixing chamber 19*b* to move the target substance and the reagent between the first mixing chamber 19*a* and the second mixing chamber 19*b*.

Next, the pressure of the gas injecting from the through-hole 7 and the pressure supply ports 18*a* and 18*d* is set about atmospheric pressure. Thereby, as shown in FIG. 4(F), the shutter-forming voids 17*a* and 17*d* and the voids of the flow channel 8, the first mixing chamber 19*a*, and the second mixing chamber 19*b* are vanished. Thereafter, gas is injected at high pressure from the injection tube 15 via the through-hole 7. Thereby, the target substance mixed with the reagent can be forwarded to the next step.

In the chip for analysis of a target substance of this Embodiment, the same magnetic particle as described in Embodiment 1 may be placed at at least one of the first mixing chamber-forming non-contact (non-bonded) area 9*a* and the second mixing chamber-forming non-bonded area 9*b*. In this case, at least one of the first mixing chamber 19*a* and the second mixing chamber 19*b* has the function of an extraction chamber.

Embodiment 4

Figure 5:
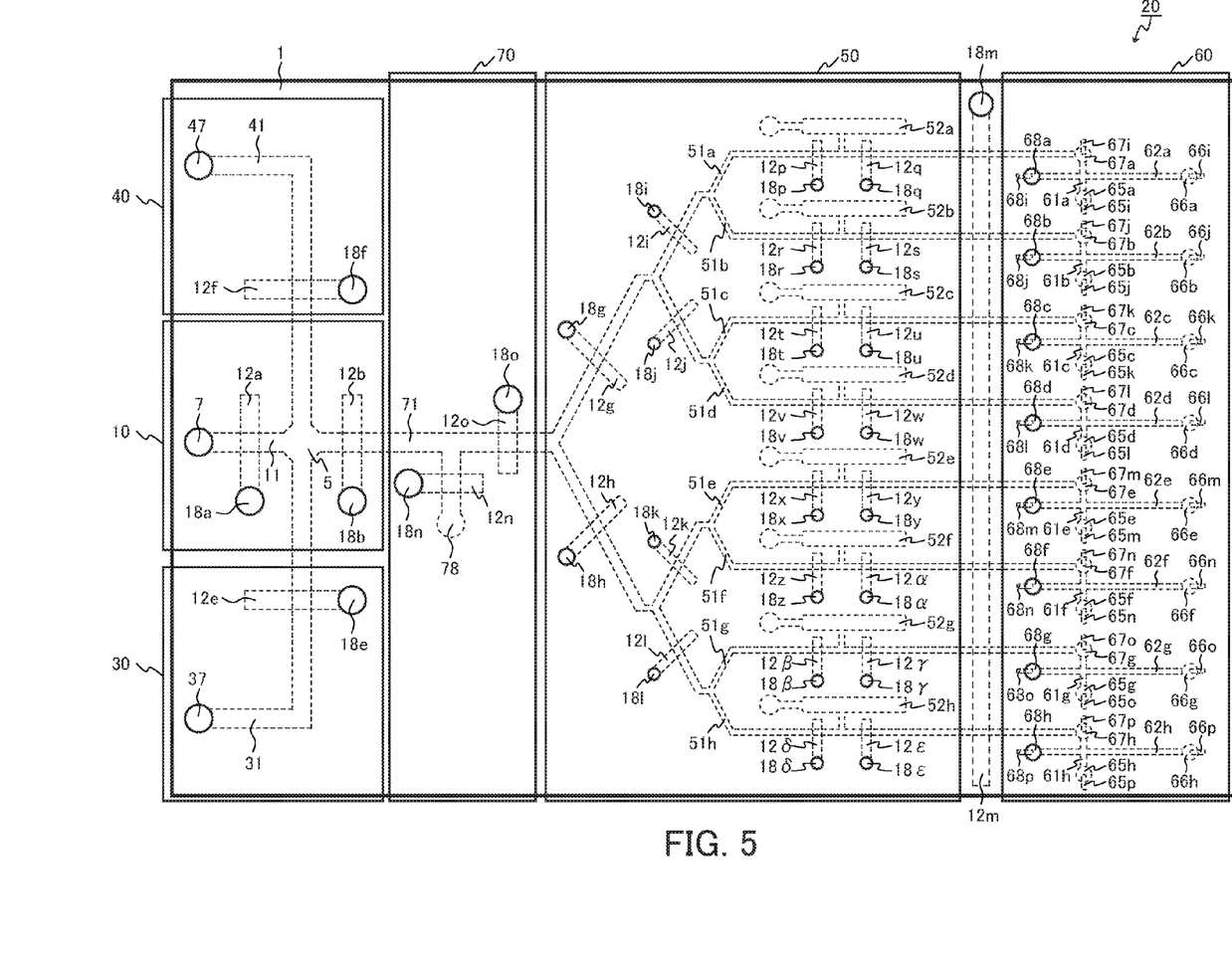
FIG. 5 is a schematic perspective plan view showing another example of the configuration of the chip for analysis of a target substance of the present invention.

FIG. 5 shows another example of the configuration of the chip for analysis of a target substance of the present invention. The aspect shown in FIG. 5 is an example and the present invention is not limited to this aspect. In FIG. 5, identical parts to those shown in FIGS. 1(A)-1(C) and 2 are indicated with identical numerals and symbols. A chip for analysis of a target substance 20 shown in FIG. 5 includes, in addition to the configuration of the chip for analysis of a target substance 10 shown in FIGS. 1(A)-1(C) and 2, a washing reagent supply portion 30, a PCR reaction reagent supply portion 40, a washing reagent recovery portion 70, a PCR amplification portion 50, a shutter-forming non-bonded area 12*m*, a pressure supply port 18*m*, and an electrophoresis analysis portion 60 as main components. The washing reagent supply portion 30, the PCR reaction reagent supply portion 40, the washing reagent recovery portion 70, the PCR amplification portion 50, and the electrophoresis analysis portion 60 each include a laminate in which the first flexible substrate 1, the second flexible substrate 2, and the third substrate 3 are laminated. The material of each of the first flexible substrate 1, the second flexible substrate 2, and the third substrate 3 is the same as that of the chip for analysis of a target substance 10 shown in FIGS. 1(A)-1(C) and 2. The shutter-forming non-bonded area 12*m* and the pressure supply port 18*m* can be formed in the same manner as the corresponding components of the chip for analysis of a target substance 10 shown in FIGS. 1(A)-1(C) and 2.

The washing reagent supply portion 30 includes a through-hole 37, a flow channel-forming non-bonded area 31, a shutter-forming non-bonded area 12*e*, and a pressure supply port 18*e* as main components. These components can be formed in the same manner as the corresponding components of the chip for analysis of a target substance 10 shown in FIGS. 1(A)-1(C) and 2. The flow channel-forming non-bonded area 31 is in contact with the extraction chamber-forming non-bonded area 5 of the chip for analysis of a target substance 10 shown in FIGS. 1(A)-1(C) and 2. In the chip for analysis of a target substance 20 of this Embodiment, the washing reagent supply portion 30 is an optional component and is not indispensable, although the chip for analysis of a target substance 20 preferably includes the washing reagent supply portion 30. In the case where the chip for analysis of a target substance 20 does not include the washing reagent supply portion 30, a washing reagent may be supplied from the through-hole 7 of the chip for analysis of a target substance 10 shown in FIGS. 1(A)-1(C) and 2.

The PCR reaction reagent supply portion 40 includes a through-hole 47, a flow channel-forming non-bonded area 41, a shutter-forming non-bonded area 12*f*, and a pressure supply port 18*f* as main components. These components can be formed in the same manner as the corresponding components of the chip for analysis of a target substance 10 shown in FIGS. 1(A)-1(C) and 2. The flow channel-forming non-bonded area 41 is in contact with the extraction chamber-forming non-bonded area 5 of the chip for analysis of a target substance 10 shown in FIGS. 1(A)-1(C) and 2. In the chip for analysis of a target substance 20 of this Embodiment, the PCR reagent supply portion 40 is an optional component and is not indispensable, although the chip for analysis of a target substance 20 preferably includes the PCR reagent supply portion 40. In the case where the chip for analysis of a target substance 20 does not include the PCR reagent supply portion 40, a PCR reagent may be supplied from the through-hole 7 of the chip for analysis of a target substance 10 shown in FIGS. 1(A)-1(C) and 2.

The washing reagent recovery portion 70 includes a flow channel-forming non-bonded area 71, shutter-forming non-bonded areas 12*n* and 12*o*, pressure supply ports 18*n* and 18*o*, and a waste tank 78 as main components. The components except for the waste tank 78 can be formed in the same manner as the corresponding components of the chip for analysis of a target substance 10 shown in FIGS. 1(A)-1(C)

and 2. The waste tank 78 can be formed in the same manner as the extraction chamber-forming non-bonded area 5 of the chip for analysis of a target substance 10 shown in FIGS. 1(A)-1(C) and 2.

In the PCR amplification portion 50, the flow channel-forming non-bonded area 11 led out from the chip for analysis of a target substance 10 shown in FIGS. 1(A)-1(C) and 2 is split into eight flow channel-forming non-bonded areas 51a to 51h via the shutter-forming non-bonded areas 12g to 12l and pressure supply ports 18g to 18l. The number of the split of the flow channel-forming non-bonded area is not limited to eight and can be increased or decreased appropriately according to a desired analysis accuracy of the target substance. The shutter-forming non-bonded areas 12g to 12l, the pressure supply ports 18g to 18l, and the flow channel-forming non-bonded areas 51a to 51h can be formed in the same manner as the corresponding components of the chip for analysis of a target substance 10 shown in FIGS. 1(A)-1(C) and 2. Eight flow channel-forming non-bonded areas 51a to 51h are respectively in contact with eight reaction tanks 52a to 52h. On the flow channel-forming non-bonded areas 51a to 51h, in the vicinity of contact points with the reaction tanks 52a to 52h, shutter-forming non-bonded areas 12p to 12z and 12α to 12∈ and pressure supply ports 18p to 18z and 18α to 18∈ are respectively formed. There is no particular limitation on the method of forming the reaction tanks 52a to 52h, and, for example, a formation method in a conventionally known PCR chip can be employed. The shutter-forming non-bonded areas 12p to 12z and 12α to 12∈ and the pressure supply ports 18p to 18z and 18α to 18∈ can be formed in the same manner as the corresponding components of the chip for analysis of a target substance 10 shown in FIGS. 1(A)-1(C) and 2.

Although it is not shown, at at least one of positions of the undersurface of the third substrate 3 directly below the reaction tanks 52a to 52h and positions of the top surface of the first flexible substrate 1 directly above the reaction tanks 52a to 52h, heating means such as heaters are placed.

The electrophoresis analysis portion 60 includes reagent tanks 67a to 67h, through-holes 68a to 68h, flow channel-forming non-bonded areas 61a to 61h and 62a to 62h, waste tanks 65a to 65h and 66a to 66h, and electrodes 67i to 67p, 68i to 68p, 65i to 65p, and 66i to 66p. The reagent tanks 67a to 67h are formed so as to be in contact with the flow channel-forming non-bonded areas 51a to 51h of the PCR amplification portion 50 via the shutter-forming non-bonded area 12m and the pressure supply port 18m. The flow channel-forming non-bonded areas 61a to 61h are formed so as to be in contact with the reagent tanks 67a to 67h at one end and be in contact with the waste tanks 65a to 65h at the other end. The flow channel-forming non-bonded areas 62a to 62h are formed so as to intersect with the flow channel-forming non-bonded areas 61a to 61h, be in contact with the through-holes 68a to 68h at one end, and be in contact with the waste tanks 66a to 66h at the other end. At the reagent tanks 67a to 67h, the through-holes 68a to 68h, and the waste tanks 65a to 65h and 66a to 66h, the electrodes 67i to 67p, 68i to 68p, 65i to 65p, and 66i to 66p are respectively placed. It is possible to apply voltages to the electrodes 67i to 67p, 68i to 68p, 65i to 65p, and 66i to 66p from above the first flexible substrate 1 or below third substrate 3. The through-holes 67a to 67h and the flow channel-forming non-bonded areas 61a to 61h and 62a to 62h can be formed in the same manner as the corresponding components of the chip for analysis of a target substance 10 shown in FIGS. 1(A)-1(C) and 2. Note here that, instead of the flow channel-forming non-bonded areas 61a to 61h and 62a to 62h, grooves formed on the third substrate 3 according to a conventionally known method may be used as flow channels. The groove has, for example, a width of about 100 μm and a depth of about 30 μm. The reagent tanks 67a to 67h and the waste tanks 65a to 65h and 66a to 66h can be formed in the same manner as the extraction chamber-forming non-bonded area 5 of the chip for analysis of a target substance 10 shown in FIGS. 1(A)-1(C) and 2. As the electrodes 67i to 67p, 68i to 68p, 65i to 65p, and 66i to 66p, conventionally known ones can be used.

Although it is not shown, at at least one of positions of the undersurface of the third substrate 3 below the flow channel-forming non-bonded areas 62a to 62h and positions of the top surface of the first flexible substrate 1 above the flow channel-forming non-bonded areas 62a to 62h, optical analysis means such as absorbance measuring apparatuses are placed.

The chip for analysis of a target substance 20 of this Embodiment may include the configuration of the chip for analysis of a target substance 10 including the mixing chamber-forming non-bonded area shown in FIG. 3 or FIG. 4 instead of the chip for analysis of a target substance 10 including the extraction chamber-forming non-bonded area 5 shown in FIGS. 1(A)-1(C) and 2. Furthermore, the chip for analysis of a target substance 20 of this Embodiment may further include a through-hole and a flow channel-forming non-bonded area for dry air supply that are formed so as to be in contact with the extraction chamber-forming non-bonded area or the mixing chamber-forming non-bonded area.

The size of the chip for analysis of a target substance 20 of this Embodiment is as follows. That is, for example, the length is in the range from 50 mm to 300 mm and the width is in the range from 20 mm to 100 mm Since the chip for analysis of a target substance of the present invention is compact as described above, it allows a small installation space.

Furthermore, the thickness of the chip for analysis of a target substance 20 of this Embodiment excluding the mechanism for generating a magnetic field in the configuration of the chip for analysis of a target substance 10 shown in FIGS. 1(A)-1(C) and 2, the heating means in the PCR amplification portion 50, and the optical analysis means in the electrophoresis analysis portion 60 is, for example, in the range from 0.5 mm to 5 mm Therefore, the chip for analysis of a target substance 20 of this Embodiment can be carried around without fixing at a predetermined space.

The chip for analysis of a target substance 20 shown in FIG. 5 is used, for example, as follows. First, in the same manner as in Embodiment 1, the target substance such as DNA is extracted from the analysis sample using the configuration of the chip for analysis of a target substance 10 shown in FIGS. 1(A)-1(C) and 2 and the washing reagent supply portion 30. The time required for extracting the target substance is, for example, about 5 minutes.

Next, the target substance that is bound to a magnetic particle is transferred to the washing reagent recovery portion 70 by supplying the PCR reaction reagent from the PCR reaction reagent supply portion 40. Next, in the washing reagent recovery portion 70, a solution obtained by removing the washing reagent from a mixture of the target substance, the washing reagent, the PCR reaction reagent, and the like is transferred to the PCR amplification portion 50. Then, PCR amplification is performed by a conventionally known method such as a method of applying a temperature cycle to the target substance and the PCR reaction reagent stored in the reaction tanks 52a to 52h. The time required for this PCR amplification is, for example, in the range from 10 minutes to 60 minutes and preferably about 15 minutes.

Next, after PCR amplification, potential differences are generated between the reagent tanks 67a to 67h and the waste tanks 65a to 65h respectively by transferring the amplification products of the target substance to the reagent tanks 67a to 67h of the electrophoresis analysis portion 60 and applying voltages to the electrodes 67i to 67p and 65i to 65p. Thereby, the flow channels formed above the flow channel-forming non-bonded areas 61a to 61h are filled with the amplification products of the target substance. Next, potential differences are generated between the through-holes 68a to 68h and the waste tanks 66a to 66h respectively by supplying an electrophoresis solution from the through-holes 68a to 68h and applying voltages to the electrodes 68i to 68p and 66i to 66p. Thereby, electrophoresis analysis is performed by introducing a small amount of amplification products of the target substance from the intersection site of the flow channel-forming non-bonded areas 61a to 61h and 62a to 62h to the flow channels formed above the flow channel-forming non-bonded areas 62a to 62h. The time required for this electrophoresis analysis is, for example, about 5 minutes. Such an electrophoresis analysis method is conventionally known.

In this manner, the chip for analysis of a target substance 20 of this Embodiment allows extraction, amplification, and analysis of a target substance such as DNA with less effort and less time such as from about 20 minutes to about 70 minutes.

The chip for analysis of a target substance 20 shown in FIG. 5 includes the PCR amplification portion 50 and the electrophoresis analysis portion 60. However, this Embodiment is not limited thereto. The chip for analysis of a target substance of this Embodiment may be the one that performs electrophoresis analysis without performing PCR amplification. Furthermore, the chip for analysis of a target substance of this Embodiment may be the one that analyzes the target substance by a method other than electrophoresis analysis such as chemiluminescence, fluorescence, or enzyme coloration. For example, analysis of the target substance such as DNA may be performed by a conventional known method such as an intercalation method or a method using a fluorescent-labeled probe.

The invention of the present application was described above with reference to the embodiments. However, the invention of the present application is not limited to the above-described embodiments. Various changes that can be understood by those skilled in the art can be made in the configurations and details of the invention of the present application within the scope of the invention of the present application.

This application claims priority from Japanese Patent Application No. 2012-063645 filed on Mar. 21, 2012. The entire subject matter of the Japanese Patent Application is incorporated herein by reference.

INDUSTRIAL APPLICABILITY

As described above, the chip for analysis of a target substance of the present invention is compact and allows analysis of a target substance such as DNA with less time and effort. The chip for analysis of a target substance of the present invention can be applied to a wide range of uses including, for example, DNA analysis in a criminal investigation.

EXPLANATION OF REFERENCE NUMERALS 1 first flexible substrate
2 second flexible substrate
3 third substrate
5 extraction chamber-forming non-bonded area
6 extraction chamber
7, 37, 47, 68a to 68h through-hole
8 flow channel
9 mixing chamber-forming non-bonded area
10 and 20 chip for analysis of a target substance
11, 31, 41, 51a to 51h, 61a to 61h, 62a to 62h, and 71 flow channel-forming non-bonded area
12a to 12z, and 12α to 12∈ shutter-forming non-bonded area
13 magnet
14 adapter
15 injection tube
16 magnetic particle
17a, 17b, 17d shutter-forming void
18a to 18z, 18α to 18∈ pressure supply port
19 mixing chamber
30 washing reagent supply portion
40 PCR reaction reagent supply portion
50 PCR amplification portion
60 electrophoresis analysis portion
65a to 65h, 66a to 66h, 78 waste tank
70 washing reagent recovery portion

The invention claimed is:

1. A chip for analysis of a target substance comprising:
a laminate; and
a magnetic field generating unit configured to generate a magnetic field,
the laminate comprising:
a first flexible substrate;
a second flexible substrate; and
a third substrate, wherein
a flow channel-forming non-bonded area is formed on a bonding surface of the first flexible substrate and the second flexible substrate in a band-like manner and an extraction chamber-forming non-bonded area having a wider band width than the flow channel-forming non-bonded area is formed at a part of the flow channel-forming non-bonded area,
the first flexible substrate comprises a through-hole that is in contact with the flow channel-forming non-bonded area,
a shutter-forming non-bonded area is formed on a bonding surface of the second flexible substrate and the third substrate in a band-like manner at a far side of the through-hole relative to the extraction chamber-forming non-bonded area such that the shutter-forming non-bonded area and the flow channel-forming non-bonded area intersect via the second flexible substrate being interposed therebetween,
at least one of both of the first flexible substrate and the second flexible substrate and the third substrate comprises a pressure supply port that comes through the substrate(s) so as to be in contact with the shutter-forming non-bonded area,
a magnetic particle that binds to a target substance is placed above the extraction chamber-forming non-bonded area,
a flow channel and an extraction chamber are formable by supplying pressure from the through-hole to raise a site above the flow channel-forming non-bonded area and a site above the extraction chamber-forming non-bonded area, the flow channel is blockable by supplying pressure from the pressure supply port to raise a site above the shutter-forming non-bonded area, the magnetic field generating unit is disposed at 1) an outer side of at least one of the first flexible substrate or the third flexible substrate, and 2) in a vicinity of an end of the extraction chamber at the opposite side of the through-hole, and the target substance that is bound to the magnetic particle is capturable by the magnetic field at least one of an undersurface of the third substrate directly below an end of the extraction chamber at the opposite side of the through-hole or a top surface of the first flexible substrate directly above an end of the extraction chamber at the opposite side of the through-hole.

2. The chip according to claim 1, further comprising:
a PCR amplification portion; and
an electrophoresis analysis portion.

3. A system for analysis of a target substance comprising:
a chip; and
a magnetic field generating unit configured to generate a magnetic field,
the chip comprising a laminate, the laminate comprising:
a first flexible substrate;
a second flexible substrate; and
a third substrate, wherein
a flow channel-forming non-bonded area is formed on a bonding surface of the first flexible substrate and the second flexible substrate in a band-like manner and an extraction chamber-forming non-bonded area having a wider band width than the flow channel-forming non-bonded area is formed at a part of the flow channel-forming nonbonded area,
the first flexible substrate comprises a through-hole that is in contact with the flow channel-forming non-bonded area,
a shutter-forming non-bonded area is formed on a bonding surface of the second flexible substrate and the third substrate in a band-like manner at a far side of the through-hole relative to the extraction chamber-forming non-bonded area such that the shutter-forming non-bonded area and the flow channel-forming non-bonded area intersect via the second flexible substrate being interposed therebetween, at least one of both of the first flexible substrate and the second flexible substrate and the third substrate comprises a pressure supply port that comes through the substrate(s) so as to be in contact with the shutter-forming non-bonded area, a magnetic particle that binds to a target substance is placed above the extraction chamber-forming non-bonded area, a flow channel and an extraction chamber are formable by supplying pressure from the through-hole to raise a site above the flow channel-forming non-bonded area and a site above the extraction chamber-forming non-bonded area, the flow channel is blockable by supplying pressure from the pressure supply port to raise a site above the shutter-forming non-bonded area, the magnetic field generating unit is disposed 1) at an outer side of at least one of the first flexible substrate or the third flexible substrate, and 2) in a vicinity of an end of the extraction chamber at the opposite side of the through-hole, and the target substance that is bound to the magnetic particle is capturable by the magnetic field at at least one of an undersurface of the third substrate directly below an end of the extraction chamber at the opposite side of the through-hole or a top surface of the first flexible substrate directly above an end of the extraction chamber at the opposite side of the through-hole.

4. The system according to claim 3, wherein the chip further comprises:
a PCR amplification portion; and
an electrophoresis analysis portion.

* * * * *